United States Patent [19]

Baghaee-Rezaee

[11] Patent Number: 5,535,740
[45] Date of Patent: Jul. 16, 1996

[54] DISPOSABLE PRESSURE GAUGE FOR RESUCITATORS

[76] Inventor: Hooshang Baghaee-Rezaee, P.O. Box 9071, Gaithersburg, Md. 20898-9071

[21] Appl. No.: 478,779

[22] Filed: Jun. 7, 1995

[51] Int. Cl.⁶ .................. A62B 7/00; G01L 7/06
[52] U.S. Cl. .................. 128/205.23; 128/205.13; 128/728; 73/729.1
[58] Field of Search .............. 73/729.1; 116/273; 128/204.18, 204.28, 205.13, 205.23, 207.14, 207.17, 728

[56] References Cited

U.S. PATENT DOCUMENTS

| | | | |
|---|---|---|---|
| 1,805,802 | 5/1931 | Browne | 73/729.1 |
| 1,946,224 | 2/1934 | Mastrangel | 73/729.1 |
| 2,834,339 | 5/1958 | Bennett et al. | 128/205.13 |
| 2,866,339 | 12/1958 | Rhodes et al. | 73/729.1 X |
| 2,940,314 | 6/1960 | Mahan | 73/729.1 X |
| 3,343,420 | 9/1967 | Kondo et al. | 73/729.1 X |
| 3,821,950 | 7/1974 | Boehringer | 128/728 |
| 4,114,458 | 9/1978 | Alinari | 73/729.1 |
| 4,241,740 | 12/1980 | Brown | 128/728 |
| 4,259,967 | 4/1981 | Vooren et al. | 128/720 |
| 4,299,236 | 11/1981 | Poirier | 128/728 |
| 4,327,741 | 5/1982 | Watson et al. | 128/728 |
| 4,425,805 | 1/1984 | Ogura et al. | 73/861.29 |
| 4,444,201 | 4/1984 | Itoh | 128/716 |
| 4,945,918 | 8/1990 | Abernathy | 128/719 |
| 5,134,996 | 8/1992 | Bell | 128/207.14 |

FOREIGN PATENT DOCUMENTS

| | | | |
|---|---|---|---|
| 815550 | 10/1951 | Germany | 73/729.1 |
| 842435 | 6/1981 | U.S.S.R. | 73/729.1 |

*Primary Examiner*—Edgar S. Burr
*Assistant Examiner*—Eric P. Raciti
*Attorney, Agent, or Firm*—Richard C. Litman

[57] ABSTRACT

A disposable pressure gauge comprises a pair of bellows members, a returning member that tends to return the bellows members to a base-line position, and a housing member that contains the pair of bellows member and returning member. The pair of bellows members and housing member have apertures disposed in such a way that the gauge measures both positive and "negative" pressure, relative to atmospheric pressure, and is pre-calibrated, inexpensive, portable and disposable, thereby avoiding a need for heavy, expensive conventional manometers that must frequently be sterilized and recalibrated. In use, the gauge is attached to an endotracheal tube, and optionally to a resuscitator bag via the endotracheal tube. Color coordination aids in use of the gauge. Attachment of the gauge will not adversely affect the operation of such a resuscitator bag.

16 Claims, 4 Drawing Sheets

DISPOSABLE PRESSURE GAUGE FOR RESUCITATORS

BACKGROUND OF THE INVENTION

1. Field of the Invention

The present invention relates generally to pressure gauges, and more specifically to pressure gauges for use with resuscitators, endotracheal tubes and related medical equipment.

2. Description of the Prior Art

During respiratory failure and total anesthesia, among other circumstances, it is necessary to provide artificial inflation of the human lungs. Artificial inflation of the lungs can be ineffective or even dangerous if proper inflation pressure is not maintained. For this reason, conventional practice includes attachment of a manometer to a resuscitator bag or respirator via a tube. In this way, pressure measurements relating to artificial inflation are obtained. Unfortunately, conventional manometers are heavy, expensive, require frequent calibration, and must be sterilized between patient-uses.

Another circumstance in which pressure must be measured is when a patient is about to be extubated (i.e. the patient is about to have a breathing tube removed from the patient's trachea). Before extubation is performed, it is necessary to ensure that a patient is capable of creating sufficient vacuum relative to atmospheric pressure to breath adequately. In this circumstance, too, conventional manometers demonstrate the failing elicited above. Because of these many undesirable manometer-characteristics, numerous attempts have been made to provide functionality of a manometer in structure not subject to all the disadvantageous features of a manometer. Yet, no such attempt provides the structure of the present invention or succeeds to the extent of the present invention.

U.S. Pat. No. 3,821,950, issued to John R. Boehringer, on Jul. 2, 1974, describes a respirometer that measures respiratory volume. The respirometer of this patent does not measure pressure produced by a respirator or resuscitator.

U.S. Pat. No. 4,241,740, issued to Joseph W. Brown, on Dec. 30, 1980, describes an incentive spirometer that measures volume of inhalations and exhalations in order to motivate proper inhalation and exhalation practice. The respirometer of this patent does not measure pressure produced by a respirator or resuscitator.

U.S. Pat. No. 4,259,967, issued to Pieter H. Vooren et al., on Apr. 7, 1981, describes a device for measuring respiratory resistance. The device of this patent does not measure pressure produced by a respirator or resuscitator.

U.S. Pat. No. 4,299,236, issued to Victor L. Poirier, on Nov. 10, 1981, describes a breathing exerciser that measures volume of inhalations and exhalations in order to motivate proper inhalation and exhalation practice. The device of this patent does not measure pressure produced by a respirator or resuscitator.

U.S. Pat. No. 4,327,741, issued to Herman L. Watson et al., on May 4, 1982, describes a device for measuring respiratory volume. The device of this patent does not measure pressure produced by a respirator or resuscitator.

U.S. Pat. No. 4,425,805, issued to Ichiro Ogura et al., on Jan. 17, 1984, describes a respiratory flowmeter that measures velocity of respired air. The device of this patent does not measure pressure produced by a respirator or resuscitator.

U.S. Pat. No. 4,444,201, issued to Ayao Itoh, on Apr. 24, 1984, describes a respiration monitor that measures velocity and pressure of respired air. The device of this patent is highly complicated, in that it also includes a computer and monitor. The device is not intended to be disposable and uses a manometer of known type.

None of the above inventions and patents, taken either singly or in combination, is seen to describe the instant invention as claimed.

SUMMARY OF THE INVENTION

A disposable pressure gauge according to the present invention comprises a pair of bellows members, a returning member that tends to return the bellows member to a base-line position, and a housing member that contains the bellows member and returning member. The bellows members and housing member have apertures disposed in such a way so that the gauge measures both positive and "negative" pressure, relative to atmospheric pressure, and is pre-calibrated, inexpensive, portable and disposable, thereby avoiding a need for heavy, expensive conventional manometers that must frequently be sterilized and recalibrated. In use, the device is attached to an endotracheal tube, and optionally to a resuscitator bag via the endotracheal tube. This attachment will not adversely affect the operation of such a resuscitator bag.

Accordingly, it is a principal object of the invention to provide a pressure gauge that is light-weight.

It is another object of the invention to provide a pressure gauge that is simple and inexpensive to manufacture, thereby enabling disposability.

It is a further object of the invention to avoid a necessity for sterilizing a manometer between patient uses.

Still another object of the invention is to provide a pressure gauge that is simultaneously useful for measuring positive pressure relative to atmospheric pressure and negative pressure relative to atmospheric pressure.

It is an object of the invention to provide improved elements and arrangements thereof in an apparatus for the purposes described which is dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
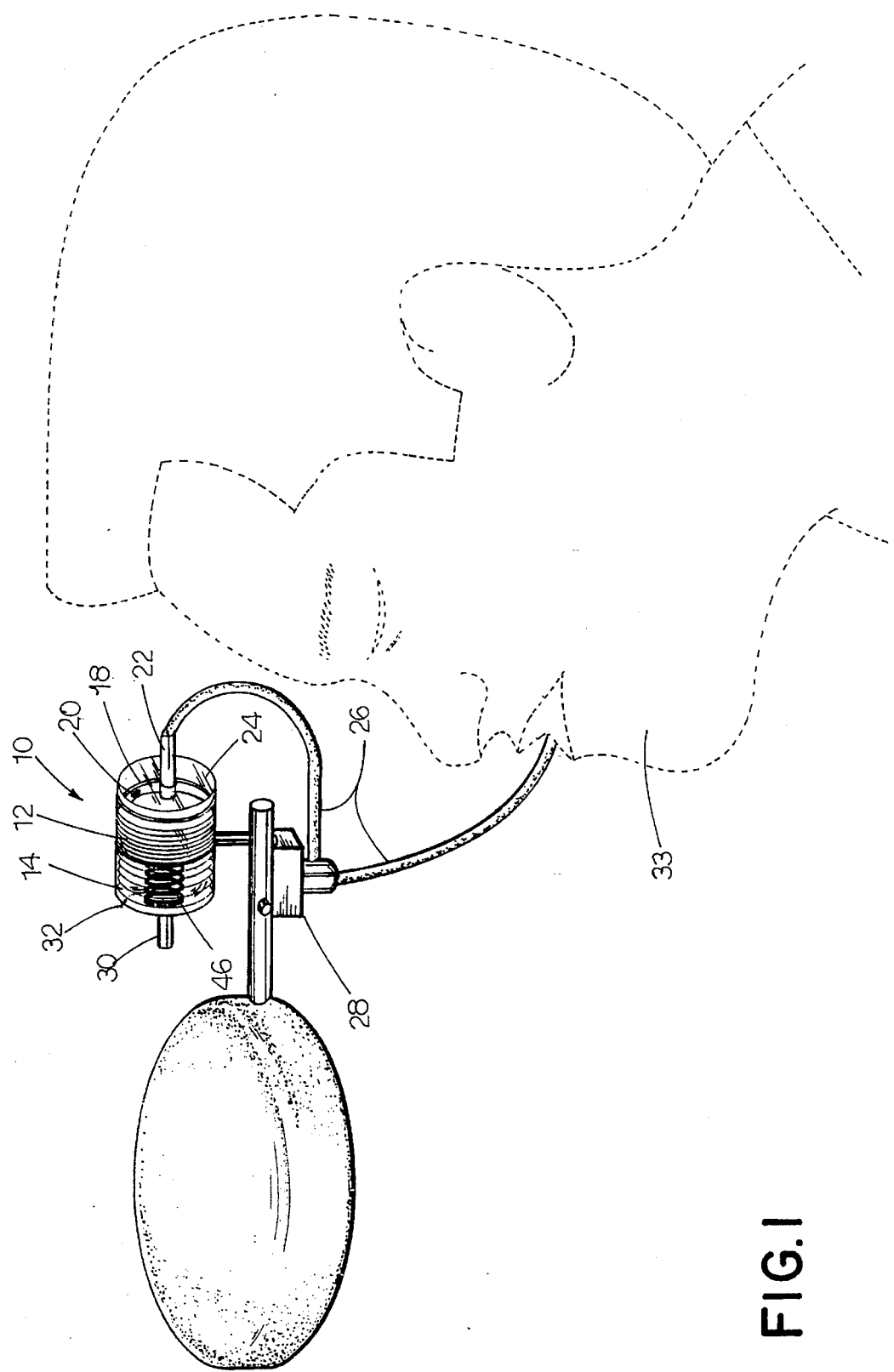
FIG. 1 is an environmental, perspective view of the present invention.

Several essential medical procedures require measurement of air pressure. These procedures include artificial lung inflation and preparation for extubation. If air pressure is not measured accurately during these procedures, the procedures will be performed ineffectively, and dangerous conditions can result, such as inadequate respiration and concomitant possibility of continued respiratory failure or failure of extubation procedure.

Referring to the drawings, the disposable pressure gauge 10 of the present invention has a pair of bellows members 12, 14, including a top bellows member 12 and a bottom bellows member 14; a returning member 46; and a housing member 18 that contains and supports the bellows members 12, 14 and the returning member 46. The bottom bellows 14 is preferably bonded at bonding point 15 to the housing member 18, by known means. In this way, the bottom bellows is immobilized relative to the housing member.

There is an equalization aperture 20 in the housing member 18 that allow air pressure within the housing 18 to remain equal to atmospheric pressure A surrounding the housing member 18. In contrast to the housing member 18, the bellows 12, 14 do not have equalization apertures; instead, the bellows have only conduit apertures 23, 31 which allow gaseous communication with conduits 22, 30. Thus, there is no gaseous communication between the bellows 12, 14 and the interior of the housing member 18.

There is a resuscitator conduit 22 projecting through a top end 24 of the housing member 18. Preferably, this resuscitator conduit 22 has a distinguishing color, preferably red. The resuscitator conduit 22 communicates with the top bellows member 12 and is dimensioned and configured to receive a source of air pressure P, such as an endotracheal tube 26 receiving air pressure P from a resuscitator 28 that is delivering air to a patient 33 for artificial respiration (not to scale). Preferably, the pressure gauge 10 is manufactured so as to be small in relation to the resuscitator 28, so as to enable convenient attachment of the pressure gauge 10 to the resuscitator, via known means.

There is also an extubation conduit 30 on a bottom end 32 of the housing member 18. Preferably, this extubation conduit 30 has a distinguishing color, preferably blue, that is noticeably distinct from that of the resuscitator conduit 22. In this way, the extubation conduit 30 and the resuscitator conduit 22 are easy to distinguish from one another. The extubation conduit 30 communicates with the bottom bellows member 14 and is dimensioned and configured to receive a source of suction (air vacuum) S, such as an endotracheal tube 26 connected to a patient who is inhaling (not depicted).

The housing member 18 is inscribed with pressure markings 50, 54 that are positioned so as to accurately indicate pressure within the bellows members 12, 14, relative to atmospheric pressure A. Units of pressure measurement to which the pressure markings 50, 54 correspond can be any known units, such as centimeters of water, Torr, pounds-per-square-inch (PSI), atmospheres, or pascals. The units are preferably centimeters of water. There is a base-line marking 38 that coincides with a marker 40 mounted on a bottom end 42 of the top bellows member 12 and a top end 44 of the bottom bellows member 14, when pressure within the bellows members 12, 14 is equal to atmospheric pressure A.

Figure 2:
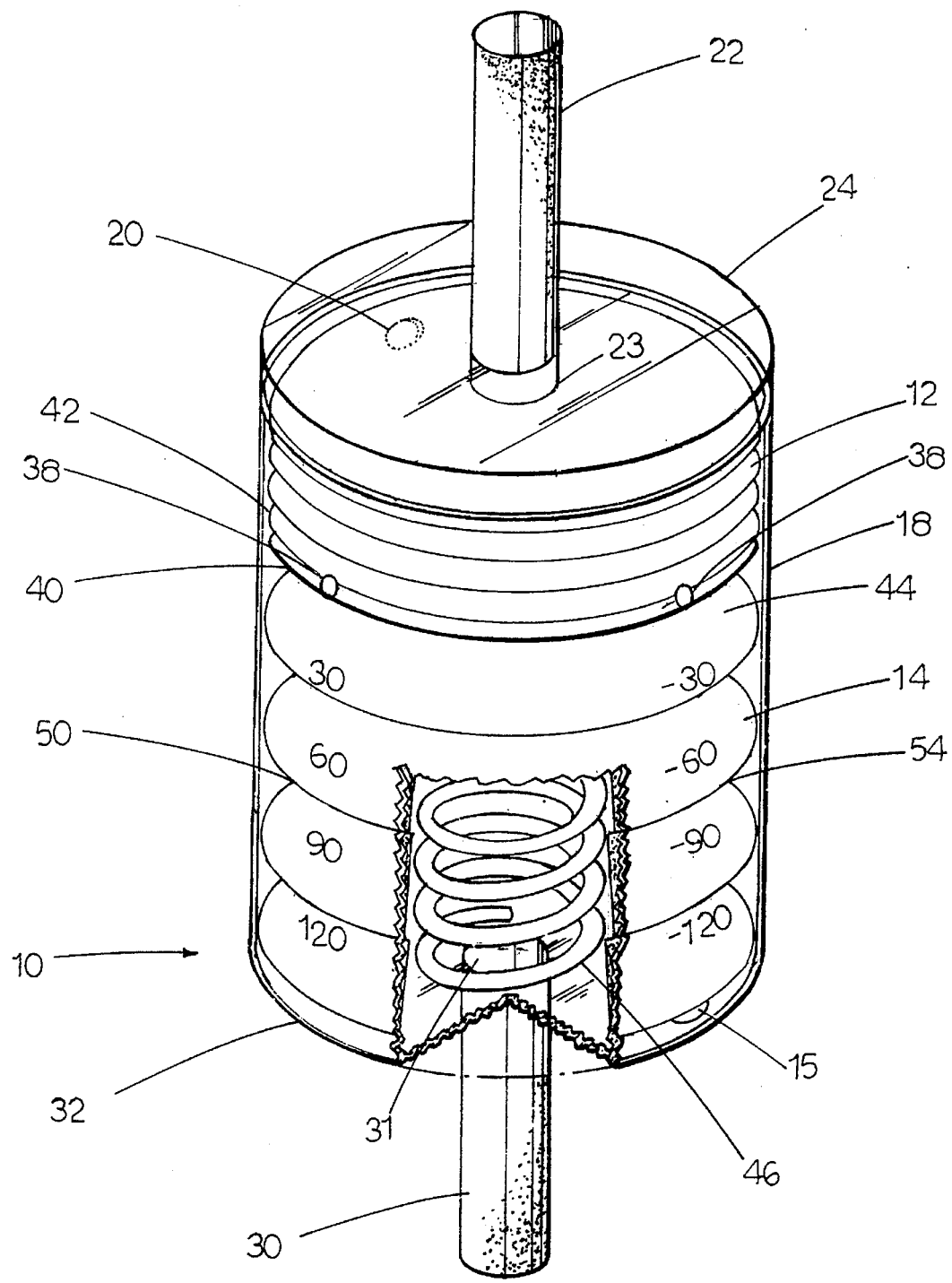
FIG. 2 is a cutaway view of the present invention when subject only to atmospheric pressure.

There is a returning member 46, preferably a spring of known type, connected to the top end 44 of the bottom bellows member 14 and a bottom end 32 of the housing member 18. This returning member 46 tends to maintain the bellows members 12, 14 in a standard position, in which the marker 40 coincides with the baseline marking 38, as shown in FIG. 2, thus indicating atmospheric pressure A.

Figure 3:
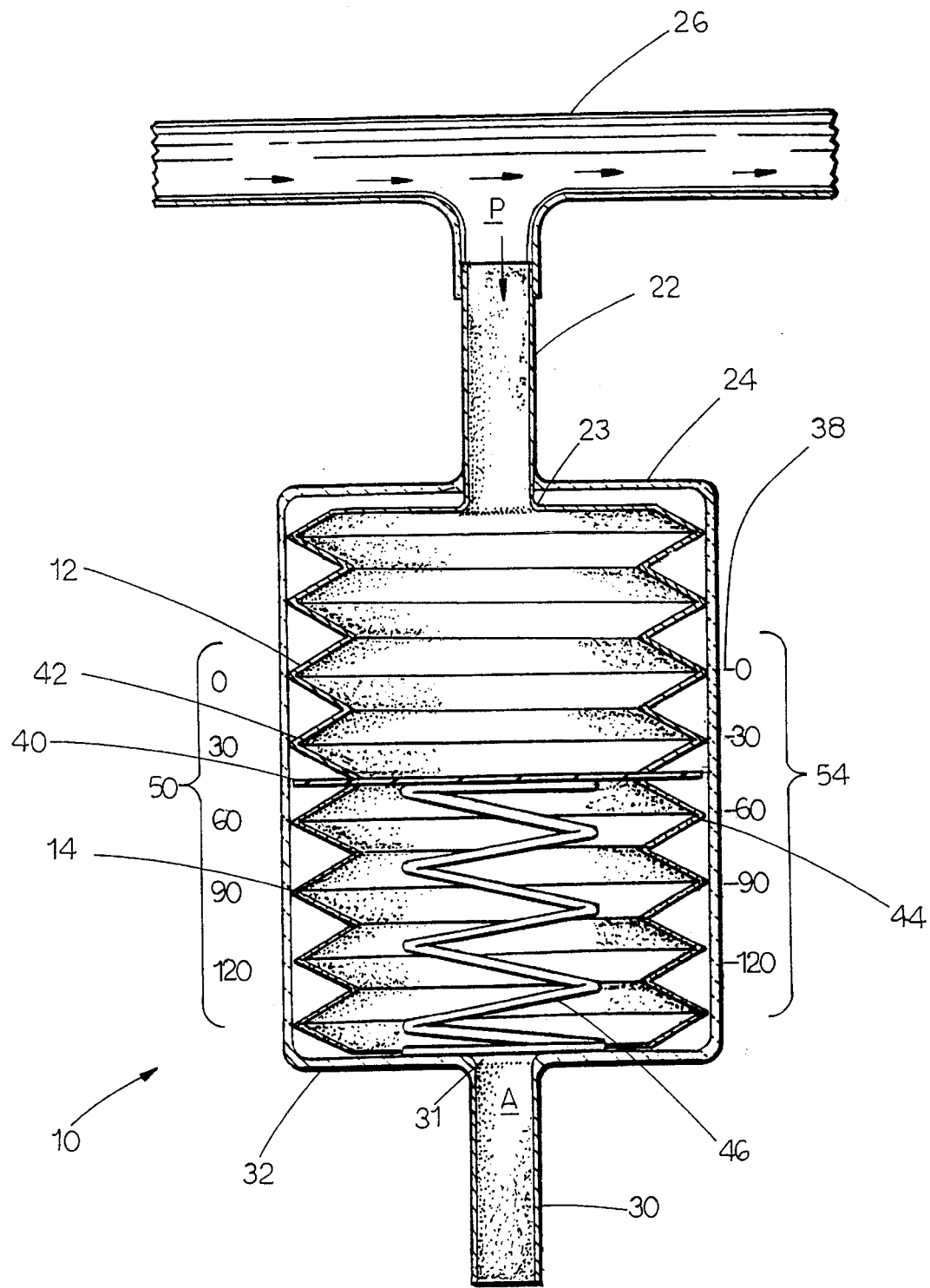
FIG. 3 is a partial environmental cross section view of the present invention when configured for use in measuring positive pressure relative to atmospheric pressure, and subject to positive pressure provided by a partially shown endotracheal tube.

When the top bellows member 12 is caused to have a high pressure P as compared to atmospheric pressure A, the top bellows member 12 tends to increase in volume. Because the top bellows member 12 is anchored to the marker 40 and the bottom bellows member 14, an increase in volume of the top bellows member 12 causes a bottom end 42 of the top bellows member 12, along with the marker 40, to move towards the bottom end 32 of the housing member 18, as shown in FIG. 3. Positive pressure markings 50 on the housing 18, below the base-line marking 38, thus indicate a "positive" pressure P, relative to atmospheric pressure A. These positive pressure markings 50 are preferably colored red. In this way, the color of the positive pressure markings 50 is the same as the color of the resuscitator conduit 22, to indicate that pressure. P applied through the resuscitator conduit 22 relates to positive pressure P relative to atmospheric pressure A.

Figure 4:
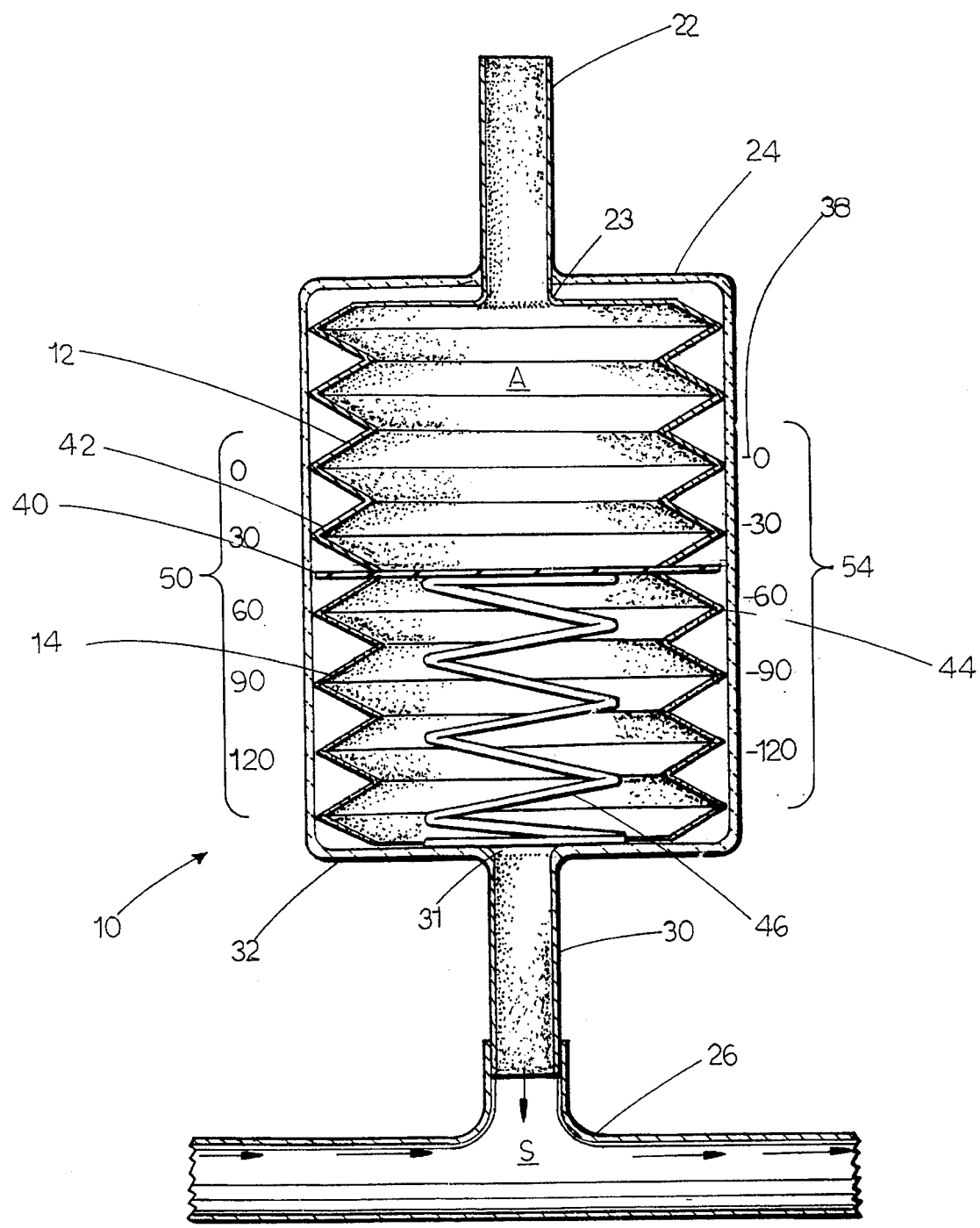
FIG. 4 is a cross section view of the present invention when configured for use in measuring negative pressure relative to atmospheric pressure, and subject to negative pressure provided by a partially shown endotracheal tube.

When the bottom bellows member 14 is caused to have a low pressure S as compared to atmospheric pressure A, the bottom bellows member 14 tends to decrease in volume. Because the bottom bellows member 14 is anchored to the marker 40 and the top bellows member 12, a decrease in volume of the bottom bellows member 14 causes a top end 44 of the bottom bellows member 14, along with the marker 40, to move towards the bottom end 32 of the housing member 18, as shown in FIG. 4. Negative pressure markings 54 on housing 18, below the base-line marking 38, thus indicate a "negative" pressure S, relative to atmospheric pressure A. These negative pressure markings 54 are preferably colored blue. In this way, the color of the negative pressure markings 54 is the same as the color of the extubation conduit 30, to indicate that suction S applied through the extubation conduit 30 relates to negative pressure S relative to atmospheric pressure A. The housing member 18 is preferably light transmissive to ensure ability to visually match the marker with pressure markings 50 and 54.

In use, the pressure gauge 10 is intended to be subject to positive pressure P, relative to atmospheric pressure A, through resuscitator conduit 22; suction S, relative to atmospheric pressure A, through extubation conduit 30; or atmospheric pressure A, when the pressure gauge is not in use. When only atmospheric pressure A is applied to the pressure gauge 10, the top bellows 12 is compressed by the returning member 46, while the bottom bellows 14 is extended, as shown in FIG. 2. When positive pressure P, relative to atmospheric pressure A, is applied through resuscitator conduit 22, the top bellows 12 is extended by the positive pressure P, while the bottom bellows 14 is compressed against the returning member 46, as shown in FIG. 3. When suction S, is applied through extubation conduit 30, the bottom bellows 14 is compressed against the returning member 46 by the suction pressure S, while the top bellows 12 is extended, as shown in FIG. 4.

The pressure gauge 10 of the present invention has among its advantages the ability to provide two very different functions. Specifically, the pressure gauge functions both in ensuring accurate artificial respiration and in ensuring a patient is strong enough to be extubated. In use, the pressure gauge 10 measures either positive or negative pressure simply by attaching the resuscitator conduit 22 or the extubation conduit 30, respectively to the pressure source to be measured, such as an endotracheal tube 26. No complex recalibrations are needed for these diverse functions; instead, the conduit attached to the pressure source need merely be switched from extubation conduit 30 to resuscitator conduit 22, or vice versa. Additionally, the gauge 10 can simply disposed of subsequent to use, with worry over cost or need for sterilization and possible transmission of disease. The pressure gauge 10 thus provides a simple, low-cost solution to a pervasive need in medical facilities for a light-weight, easy-to-use pressure gauge.

It is to be understood that the present invention is not limited to the sole embodiment described above, but encompasses any and all embodiments within the scope of the following claims.

I claim:

1. A disposable pressure gauge, comprising:

a top bellows member having a bottom end;

a bottom bellows member having a top end;

a returning member having a first end and a second end, said first end being connected to said top end of said bottom bellows member, said returning member being dimensioned and configured to return said bottom bellows member to a base-line position;

a housing member having a top end and a bottom end, said second end of said returning member being connected to said bottom end of said housing member, said housing member being dimensioned and configured to contain and support said top bellows member, said bottom bellows member, and said returning member; and an extubation conduit projecting through said bottom end of said housing member and communicating with said bottom bellows member.

2. The disposable pressure gauge according to claim 1, further including a resuscitator conduit projecting through said top end of said housing member and communicating with said top bellows member.

3. The disposable pressure gauge according to claim 1, further including an equalization aperture in said housing member, whereby pressure inside said housing member is maintained at atmospheric pressure.

4. The disposable pressure gauge according to claim 1, further including a marker disposed between said top bellows member and said bottom bellows member, said marker being connected to said bottom end of said top bellows member and to said top end of said bottom bellows member.

5. The disposable pressure gauge according to claim 4, further including visible inscriptions disposed on said housing member, said inscriptions including pressure indicia.

6. The disposable pressure gauge according to claim 5, wherein said indicia include a base-line marking that coincides visually with said marker when pressure within said top bellows member and said bottom bellows member is equal to atmospheric pressure.

7. The disposable pressure gauge according to claim 5, wherein said indicia include positive pressure markings, each of said positive pressure markings coinciding visually with said marker when pressure within said top bellows member is greater than atmospheric pressure by an amount equal to each of said positive pressure markings with which said marker coincides.

8. The disposable pressure gauge according to claim 5, wherein said indicia include negative pressure markings, each of said negative pressure markings coinciding visually with said marker when pressure within said bottom bellows member is less than atmospheric pressure by an amount equal to each of said negative pressure markings with which said marker coincides.

9. A disposable pressure gauge, comprising:

a top bellows member having a bottom end;

a bottom bellows member having a top end;

a returning member having a first end and a second end, said first end being connected to said top end of said bottom bellows member, said returning member being dimensioned and configured to return said bottom bellows member to a base-line position;

a housing member having a top end and a bottom end, said second end of said returning member being connected to said bottom end of said housing member, said housing member being dimensioned and configured to contain and support said top bellows member, said bottom bellows member, and said returning member;

a marker disposed between said top bellows member and said bottom bellows member, said marker being connected to said bottom end of said top bellows member and to said top end of said bottom bellows member;

visible inscriptions disposed on said housing member, said inscriptions including pressure indicia including a base-line marking that coincides visually with said marker when pressure within said top bellows member and said bottom bellows member is equal to atmospheric pressure, said indicia further including positive pressure markings, each of said positive pressure markings coinciding visually with said marker when pressure within said top bellows member is greater than atmospheric pressure by an amount equal to a positive pressure marking with which said marker coincides, said indicia further including negative pressure markings, a negative pressure markings coinciding visually with said marker when pressure within said bottom bellows member is less than atmospheric pressure by an amount equal to said a negative pressure marking with which said marker coincides;

a resuscitator conduit projecting through said top end of said housing member and communicating with said top bellows member;

an extubation conduit projecting through said bottom end of said housing member and communicating with said bottom bellows member; and an equalization aperture in said housing member, whereby pressure inside said housing member is maintained at atmospheric pressure.

10. The disposable pressure gauge, according to claim 9, wherein said positive pressure markings and said negative pressure marking each have a color, each of said color being distinguishable from each other of said color.

11. The disposable pressure gauge, according to claim 9, wherein said color of said positive pressure markings is red and said color of said negative pressure markings is blue.

12. The disposable pressure gauge, according to claim 9, wherein said bottom end of said bottom bellows is bonded to said housing member.

13. The disposable pressure gauge, according to claim 9, wherein said resuscitator conduit and said extubation conduit each have a color, each of said color being distinguishable from each other of said color.

14. The disposable pressure gauge, according to claim 13, wherein said color of said resuscitator conduit is red and said color of said extubation conduit is blue.

15. The disposable pressure gauge, according to claim 9, wherein:

said resuscitator conduit has a red color and said extubation conduit has a blue color; and said positive pressure markings have a red color and said negative pressure marking have a blue color.

16. The disposable pressure gauge, according to claim 15, wherein said housing member is transmissive to visible light.

* * * * *